United States Patent [19]

Seal

[11] Patent Number: 4,483,189
[45] Date of Patent: Nov. 20, 1984

[54] FLUSHING APPARATUS FOR A DRILLING MUD TESTING SYSTEM

[75] Inventor: Henry Seal, Arlington, Tex.

[73] Assignee: Mobil Oil Corporation, New York, N.Y.

[21] Appl. No.: 518,336

[22] Filed: Jul. 29, 1983

[51] Int. Cl.³ .......................................... E21B 47/00
[52] U.S. Cl. ...................................... 73/155; 73/153
[58] Field of Search .................. 73/155, 153, 61.4, 55; 239/112, 113; 60/593

[56] References Cited

U.S. PATENT DOCUMENTS 3,230,761 1/1966 Sanders .......................... 73/119 A
3,286,510 11/1966 Parker ................................ 73/61.4

Primary Examiner—John W. Caldwell, Sr.
Assistant Examiner—Ellwood G. Harding, Jr.
Attorney, Agent, or Firm—Alexander J. McKillop; Michael G. Gilman; Charles J. Speciale

[57] ABSTRACT

A system for testing the parameters of drilling mud has a flush pump for periodically flushing drilling mud from the components of the system. The flush pump includes a piston driven by a source of pressurized air selectively applied to one side to pressurize flush water and to the other side to retract the piston and to draw another volume of flush water from the source. A solenoid valve between the flush pump and viscosity measuring tubes in the system connects the volume of pressurized flush water in the pump to a tap of the measuring tubes by displacement of the piston.

7 Claims, 3 Drawing Figures

FLUSHING APPARATUS FOR A DRILLING MUD TESTING SYSTEM

BACKGROUND OF THE INVENTION

This invention relates to apparatus for periodically flushing drilling mud from a system for testing the parameters of drilling mud, and more particularly, to a flush pump which supplies a volume of pressurized flush water upon demand.

In the drilling of wells, such as oil or gas wells, by the rotary method, a drilling mud is circulated from the surface of the earth to the drill bit and back to the surface again for the purposes of cooling the drill bit, removing earth cuttings from the bore hole, and imposing a hydrostatic pressure on the drilled earth formations to prevent flow of fluid therefrom into the well bore hole. In a drilling mud containing water and clay, the rheological properties of plastic viscosity, gel strength, and yield point, which must be maintained within limits in order that the drilling fluid remain pumpable and perform its desired functions, depend largely upon the concentration of clay solids and the extent to which the clay solids are hydrated by and dispersed within the water contained in the fluid.

Drilling muds are used under a wide variety of conditions which require that different compositions be used. For example, where the well bore hole passes through formations containing clay, the clay admixes with the drilling fluid and this clay is hydrated by and dispersed by the water in the drilling fluid, thereby increasing the concentration of dispersed clay solids. The increase in the concentration of dispersed clay solids deleteriously affects the rheological properties of the drilling fluid. Accordingly, where control of rheological properties is important, the drilling fluid should have a minimum change in such properties with increasing concentrations of clay solids.

Usually, drilling muds are thixotropic, i.e., they increase in gel strength when quiescent and decrease in gel strength when agitated, whereby the cuttings may be readily separated from the drilling fluid at the surface of the earth and, in the event circulation of drilling fluid is stopped for any reason, the cuttings will be properly suspended by the drilling fluid within the well and not sink to the bottom thereof with resultant danger of sticking drill pipe. The thixotropic properties of a drilling mud are ordinarily imparted thereto by virtue of employing as one of the constituents of the drilling fluid a clay such as bentonite. Since one of the functions of a drilling fluid is to impose a hydrostatic pressure on the formations penetrated by the well, it is desirable that the drilling fluid have a high density, and density of a drilling mud is increased by adding thereto a weighting agent such as barite. Drilling muds also often contain caustic soda which is added thereto to control viscometric properties, solubilize certain constituents, reduce corrosion, inhibit fermentation of organic additives, reduce the effect of contaminants picked up during drilling and to effect other results depending on the type of drilling fluid being employed.

Another property desired in a drilling fluid is that of resisting solidification of high temperature. With increasing depth of the well, the bottom hole temperature increases. In many wells, these temperatures exceed 300° F. With aqueous drilling fluids, high temperatures induce cementation reactions between clay minerals and various drilling fluid additives. As a result, the drilling fluid tends to attain excessively high gel strengths and to solidify. With solidification, excessively high pump pressures are required to break circulation with the result that often loss of the drilling fluid occurs by being forced into permeable formations. Additionally, solidification of the drilling fluid can prevent logging tools from reaching the bottom of the well.

Frequently, during the drilling of a well, drilling conditions change. Changes in temperature occur. The character of the formations being drilled may change, as, for example, salt may be encountered. Each change in drilling conditions can affect the properties of the drilling fluid. Frequently, to counteract the effect of the changed drilling conditions on the properties of the drilling fluid a change in the composition or character of the drilling fluid is required.

The foregoing and other considerations, dictate that drilling muds be tested under conditions which closely approximate conditions which would be encountered during drilling. By adding different additives, and by subjecting the drilling mud to various conditions of temperature and pressure, a determination can be made as to whether the mud will perform adequately under actual drilling conditions.

In such a testing system, drilling mud tends to cake and may block critical components, particularly in the viscosity measuring instruments. It is desirable to periodically flush these components with cleansing water. Prior art pumps do not have the capability delivering a pressurized volume of flush water on demand. For example, a commercially available Haskell pump, Model MS-12, continuously delivers controlled volumes of fluid, but cannot deliver a single controlled volume upon demand. It is an object of the present invention to provide a flush pump for a system for testing the parameters of drilling mud.

It is another object of the invention to provide a flush pump which will deliver a given volume of pressurized flush water to the system upon demand.

RELATED APPLICATIONS

The following related applications are incorporated by reference herein: "CONTROLLED HEATER FOR DRILLING MUD TESTING SYSTEM", Quigley and Russell, Ser. No. 518,568, filed July 29, 1983; "PREPARATION UNIT FOR A DRILLING MUD TESTING SYSTEM", Prior, Ser. No. 518,569, filed July 29, 1983; "DRILLING MUD TESTING SYSTEM HAVING A THERMALLY ISOLATED PUMP", Prior, Ser. No. 518,565, filed July 29, 1983.

SUMMARY OF THE INVENTION

In accordance with the present invention, a flush pump has a piston driven by a source of pressurized air which is selectively applied to one side of the piston. A volume of flush water on the other side of the piston is pressurized by the air. A solenoid valve connected between the flush pump and the testing system is operated to connect the volume of pressurized flush water to the measuring instruments by displacement by the piston. Valves are actuated by operation of the piston to connect the source of pressurized air to one side of the piston during displacement and to the other side of the piston after displacement in order to retract the piston and to draw another volume of flush water into the pump.

The foregoing and other objects, features and advantages of the invention will be better understood from the following more detailed description and appended claims.

SHORT DESCRIPTION OF THE DRAWINGS

DESCRIPTION OF THE PREFERRED EMBODIMENT

Figure 1:
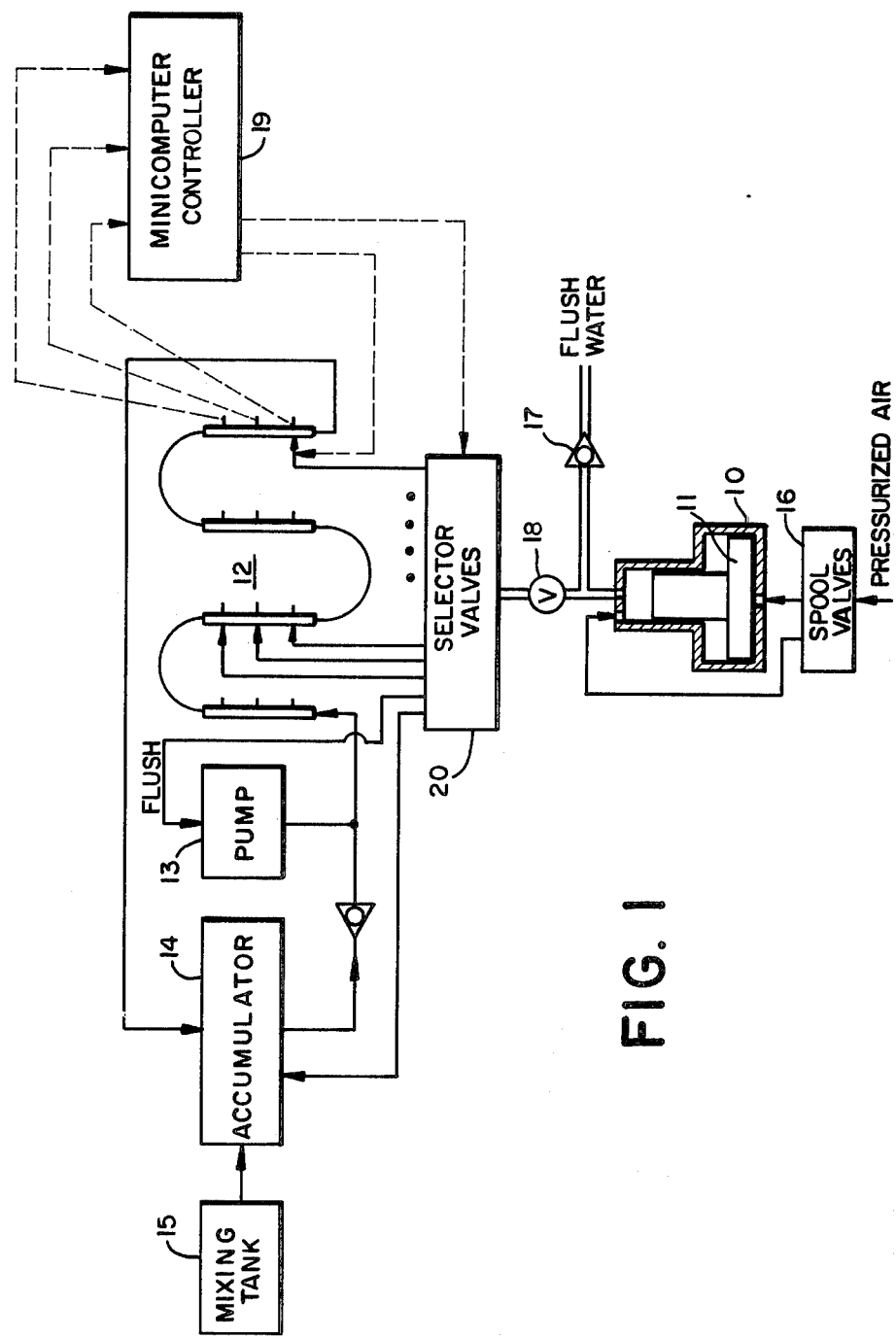
FIG. 1 shows the system for testing the parameters of drilling mud and the flushing apparatus of this invention.

Referring to FIG. 1, flush pump 10 has a piston 11 for supplying a given volume of pressurized water to selected points in the drilling mud testing system. This system includes viscosity measuring tubes 12 and other instruments for measuring the parameters of drilling mud which is pumped in a recirculating loop by pump 13. Viscosity measuring tubes 12 include pressure taps so that the pressure drop across two of the taps can be determined as a measure of viscosity. The system also includes an accumulator 14 for pressurizing the mud and a tank 15 for mixing the mud which is to be tested. The system is more fully described in the aforementioned Prior applications.

Piston 11 is driven by a source of pressurized air which is applied through the spool valves 16 to one side or the other of the piston. A source of flush water is supplied through check valve 17 to the other side of the piston, where it is pressurized by pressurized air applied to the bottom of the piston. The bottom of the piston has a larger area than the area of the side which pressurizes the flush water to amplify the air pressure to a higher water pressure.

A solenoid valve 18 is connected between the flush pump 10 and the measuring section of the system. When a start button on the controller 19 is manually operated, the solenoid valve 18 is energized to connect the volume of pressurized flush water in the pump 10 to the measuring means by displacement by the piston 11. Selector valves 20 are opened by controller 19 to provide for a flow of water through one of the pressure taps on the viscosity measuring tubes 12. Alternatively, the volume of flush water is directed to another area of the system which is to be cleansed of drilling mud. The valves which supply pressurized flush water to selected parts of the system are more fully shown in the aforementioned Prior applications.

Figure 2:
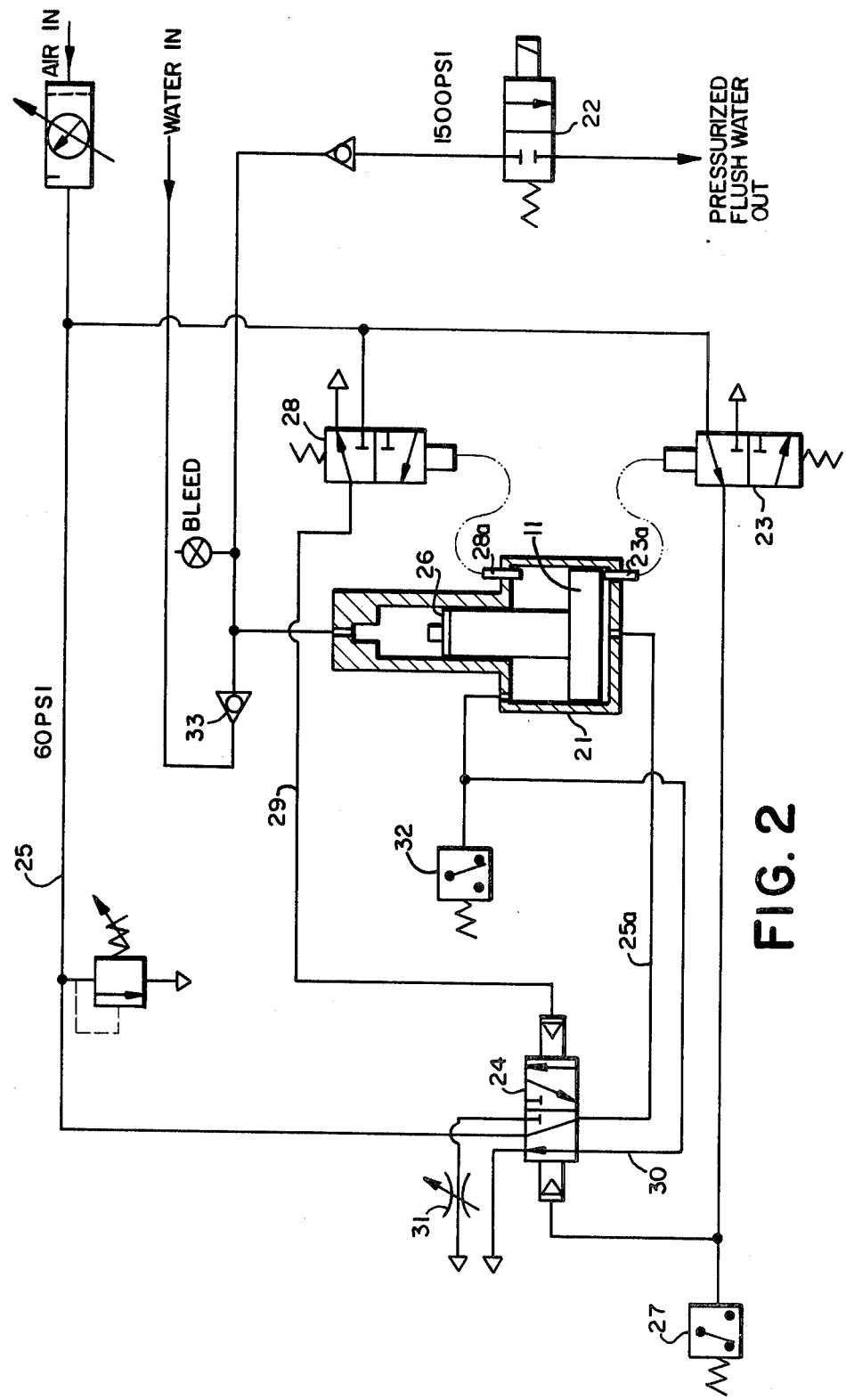
FIG. 2 shows the flush pump and associated valves and hydraulic connections.

FIG. 2 shows the spool valves which are actuated by the piston 11 for connecting the source of pressurized air to one side of the piston during displacement and to the other side of the piston after displacement to retract the piston and to draw another volume of flush water from the source. These valves include first and second spool valves 23 and 28 which have actuating rods 23a and 28a, respectively, operated by the piston 11 and a third spool valve 24 which directs pressurized air to the bottom of piston 11 during displacement and to the top of piston 11 to retract it. These spool valves are of a type which is commercially available, such as the model RR2 spool valve available from AAA Products Company. They connect different input ports with different output ports in the actuated and unactuated condition. For example, valve 23 is shown in its actuated condition in which an inlet port on the right is connected to an outlet port on the left. When the valve is relaxed, the exhaust port on the right is connected to the outlet port on the left. Similarly, valve 28 is shown in its unactuated condition in which an exhaust port on the right is connected to an outlet port on the left. In the actuated condition, the inlet port on the right is connected to the outlet port on the left.

Figure 3:
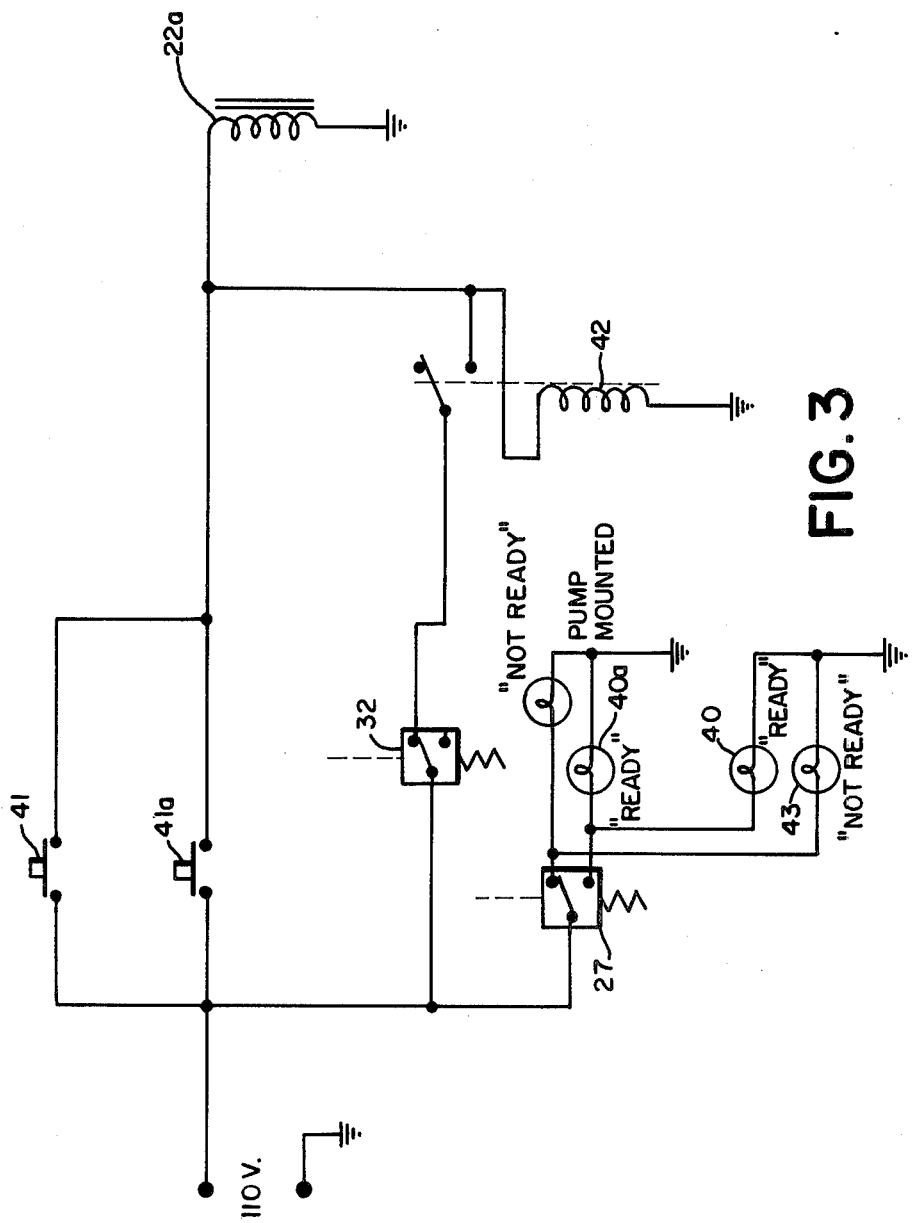
FIG. 3 is an electrical schematic diagram of the flush pump.

Referring now to FIGS. 2 and 3, the operation is as follows. In the "Ready" position, the air piston 11 is completely retracted against the cylinder head 21, valve 22 is closed and valve 23 is shifted by the actuating rod 23a in contact with the air piston to the position in which it is shown. 60 psi air is directed through valve 23 and applied against the left side of spool valve 24 shifting it to the position shown. This allows pressurized air to be applied through lines 25 and 25a to push against the piston. The ram 26, connected to the piston, then pressurizes the flush water to 1500 psi. Since valve 22 is closed, no motion can occur in the system at this point.

Pressure switch 27 senses pressure and electrically lights the "Ready" indicator 40 (FIG. 3) on the console control board and the indicator 40a on the pump.

In preparation for flushing, the desired pressure tap must be isolated from the console control board. The pump has been sized to inject a 6.25 cc stroke up to a maximum system pressure of 1500 psi. To take full advantage of the pump stroke only one tap should be flushed at a time.

To fire the ram, the console mounted start button 41 (FIG. 3) or the pump mounted start button 41a, is pressed. This energizes solenoid 22a of valve 22 allowing flow into the viscometer loop. To insure that valve 22 stays open for a full stroke, a latching relay 42 (FIG. 3) is also energized by the start button and supplies continuous power to valve 22. As the piston 11 moves away from the cylinder head 21, valve 23 moves to its unactuated position, thus removing air pressure from the left side of pilot operated spool valve 24.

At the top of the piston stroke, valve 28 is actuated by the actuating rod 28a operated by the piston 11. Pressurized air is directed through line 29 to the right side of valve 24, causing the spool to shift. Pressurized air is now directed through valve 24 and line 30 to the top of the piston. The head side of the piston is allowed to exhaust through line 25a and metering valve 31. Pressure switch 32 senses the air pressure and breaks electrical continuity to the latching relay and solenoid valve 22. Valve 22 closes, and fresh water is drawn from the reservoir through a check valve 33, as the ram retracts.

As the piston 11 beings to retract, valve 28 is relaxed when the piston releases actuating rod 28a. This allows the right side of valve 24 to exhaust through line 29. The spool of valve 24 does not shift at this time since both sides of the spool are open to atmosphere.

At the end of retraction, the piston 11 actuates valve 23 which applies pressure to the left side of valve 24 causing it to shift back to its original "Ready" position. Pressure is now redirected through 25a to the underside of the piston 11 and the top is allowed to exhaust.

Since valve 22 was allowed to close at the beginning of the retraction stroke, the hydraulic portion of the system is once again dead-headed and motion stops. With valve 23 held open by the actuating rod 23a, pressure switch 27 is once again subjected to pressure and causes the "Ready" indicator 40 to come on and the "Not Ready" light 43 to go off.

While a particular embodiment of the invention has been shown and described, various modifications are within the true spirit and scope of the invention. The appended claims are, therefore, intended to cover all such modifications.

What is claimed is:

1. A system for testing the parameters of drilling mud with apparatus for periodically flushing said drilling mud from components of said system comprising:
   measuring means for testing the parameters of said drilling mud;
   a flush pump having a piston driven by a source of pressurized air selectively applied to one side of said piston, said flush water being pressurized by said pressurized air;
   a solenoid valve between said flush pump and said measuring means to selectively connect the volume of pressurized flush water in said pump to said measuring means by displacement by said piston;
   first and second spool valves having actuating rods respectively operated by said piston in its retracted position and in its displaced position; and
   a third spool valve operated by pressurized air supplied through said first valve to set said third valve in one position when said piston is displaced and supplied through said second spool valve to said third spool valve to move it to another position when said piston is displaced;
   said source of pressurized air being connected to said one side of said piston during displacement and to the other side of said piston after displacement by said third spool valve.

2. The system recited in claim 1 wherein said piston has a larger area on said one side than on said other side to pressurize said flush water to a higher pressure than the pressure of said source of air.

3. The system recited in claim 1 further comprising:
   manually operated switch for operating said solenoid valve to flush said system.

4. The system recited in claim 3 further comprising:
   a latching relay operated when said manually operated switch is closed to apply power to said solenoid valve during the displacement stroke of said piston.

5. The system recited in claim 4 further comprising:
   a pressure switch connected to sense air pressure applied to the other side of said piston after displacement, said pressure switch interrupting the application of power to said latching relay when pressurized air is applied to said piston to retract it.

6. The system recited in claim 1 further comprising:
   a pressure-actuated switch for sensing when said piston is in its retracted position ready to supply flush water to said system; and
   indicating means operated by said pressure actuated switch for indicating the condition of said flush pump.

7. The system recited in claim 1 wherein said measuring means includes viscosity testing tubes having pressure taps; and
   valves for selectively directing flush water to one of said taps to remove drilling mud from the selected taps.

* * * * *